United States Patent [19]
Horvath et al.

[11] Patent Number: 5,966,827
[45] Date of Patent: Oct. 19, 1999

[54] METHOD AND APPARATUS FOR MEASURING PELVIC SYMMETRY

[76] Inventors: Laura Horvath, 164 Osner Dr.; David Jirmenez, 145 Copeland Rd. F-9, both of Atlanta, Ga. 30342

[21] Appl. No.: 08/642,763

[22] Filed: May 6, 1996

[51] Int. Cl.$^6$ .................................................. G01B 3/02
[52] U.S. Cl. .............................................. 33/512; 128/781
[58] Field of Search ............................... 33/511, 512, 534, 33/1 N; 128/774, 781

[56] References Cited

U.S. PATENT DOCUMENTS

| | | | |
|---|---|---|---|
| 2,810,964 | 10/1957 | Engelbert | 33/174 |
| 3,020,639 | 2/1962 | Karpovich | 33/511 |
| 3,331,134 | 7/1967 | Jackson et al. | 33/534 |
| 4,201,226 | 5/1980 | Phillips | 33/512 |
| 4,846,194 | 7/1989 | Sabia | 33/512 |
| 4,872,268 | 10/1989 | Perrault | 33/512 |
| 5,082,003 | 1/1992 | Lamb | 33/512 |
| 5,156,162 | 10/1992 | Gerhardt | 33/512 |
| 5,329,933 | 7/1994 | Graf | 33/512 |

Primary Examiner—Daniel G. DePumpo
Attorney, Agent, or Firm—Steven C Stewart

[57] ABSTRACT

A method and apparatus for measuring pelvic symmetry to aid in diagnosing and treating lower back pain. A first angle is measured between the horizon and a axis extending between a left ASIS and a left PSIS and simultaneously compared against a second angle corresponding to the angle between the horizon and an axis extending between a right ASIS and a right PSIS. The angle of a line extending through points bisecting each of the axis and the horizon is also measured. The angles are then compared against prior measurements or norms to assess posture and pelvic position in order to document progress of lower back pain treatment.

10 Claims, 1 Drawing Sheet

METHOD AND APPARATUS FOR MEASURING PELVIC SYMMETRY

BACKGROUND OF THE INVENTION

This invention relates to a method and apparatus for aiding in the diagnosing and treating lower back pain by measuring the relationship between two sides of the bodies' pelvic bone, and more particularly to a method for measuring the symmetry of these two bones along the sacroiliac joint.

Distortions of the spine are principally the result of faulty postural habits, trauma or injury of some sort, or congenital deformities. These distortions and particularly distortion of the pelvic structure can result in displacement of the innominate bones and sacrum from the norm, which is believed to be the source of some lower back pain.

When diagnosing and treating lower back pain, it has been observed that there is a relationship between the asymmetry of the pelvic bone and symptoms of such pain. This asymmetry is possibly caused by incorrect shurling of the muscle groups in the lower back and mechanical problems in joints around the pelvic bone. Examples of mechanical problems include one muscle group being shorter or longer than the other resulting in the pelvis being askew. When the pelvis is askew, problems have been noticed in the lumbar vertebrae which disrupt mechanics of the skeleton.

Pain in the lower back caused by pelvic asymmetry is treated by convention methods, such as exercising the muscles around the pelvis and applying heat to the joint. The purpose of these treatments is to expand the muscles around the pelvis to correct the symmetry. It is believed that by correcting this symmetry, lower back pain is alleviated.

One method of detecting this asymmetry, also referred to as an obliquity, is by measuring the angle of the line between two strategic points along the pelvic bone, namely the posterior superior iliac spine (PSIS) and the anterior superior iliac spine (ASIS) on one side of the body with respect to horizontal, when a person is in the upright position, and then comparing this angle with line on the other side of the body. However, a person must not move when these angles are measured or the measurement may be in error. Other devices for detecting asymmetry, such as shown in U.S. Pat. No. 2,810,964 is by placing rods against the body at different points, and then measuring the height of these different points. However a drawback of this device is that it does not indicate the angle of an axis through the ASIS and the PSIS with respect to the horizon on both the left and right side of the body. Also this device does not indicate an accurate angle of tilt of the body about the angle when detected on the left and right side of the body and cannot be easily transported.

SUMMARY OF THE INVENTION

An object of this invention is to provide an improved method and apparatus for detecting asymmetry of the pelvic structure.

Another object of this invention is to easily measure change the pelvic bones by noting the of position of the ASIS and PSIS to diagnose and treat lower back pain.

It is also an object of this invention to track symmetry of the pelvis.

It is a further object of this invention to indicate the angle of an axis through the ASIS and the PSIS with respect to the horizon on both the left and right side of the body.

These and other objects are provided with an apparatus for measuring pelvic symmetry. The apparatus includes a left bracket that connects between a left anterior superior iliac spine (ASIS) and a left posterior superior iliac spine (PSIS). On the bracket is an indication device which indicates a first angle of a first axis extending between the left ASIS and left PSIS and the horizon in the sagittal plane. A right bracket is coupled to the left bracket and connects between a right ASIS and a right PSIS. On the right bracket is a angle indication device which indicates an angle of an axis extending between of the right ASIS and right PSIS and the horizon simultaneously while measuring the second angle. A center bracket couples the left bracket to the right bracket means for measuring the angle of a line extending between the point where the center bracket couples to the left bracket and the point where the center bracket couples to the right bracket and the horizon in the frontal plane. This device indicates the symmetry of the pelvis while simultaneously indicating a pelvic tilt.

In another embodiment of the invention, a method for measuring pelvic symmetry is shown. In this method, a first angle of a left axis extending through the left ASIS and left PSIS with respect to the the horizon is measured. Simultaneously a second angle of a right axis extending through the right ASIS and right PSIS is recorded when measuring the first angle. Preferably the angle of a line extending between a point bisecting the left axis and a point bisecting the right axis with respect to the horizon is measured in a frontal plan.

BRIEF DESCRIPTION OF THE PREFERRED EMBODIMENT

Figure 1:
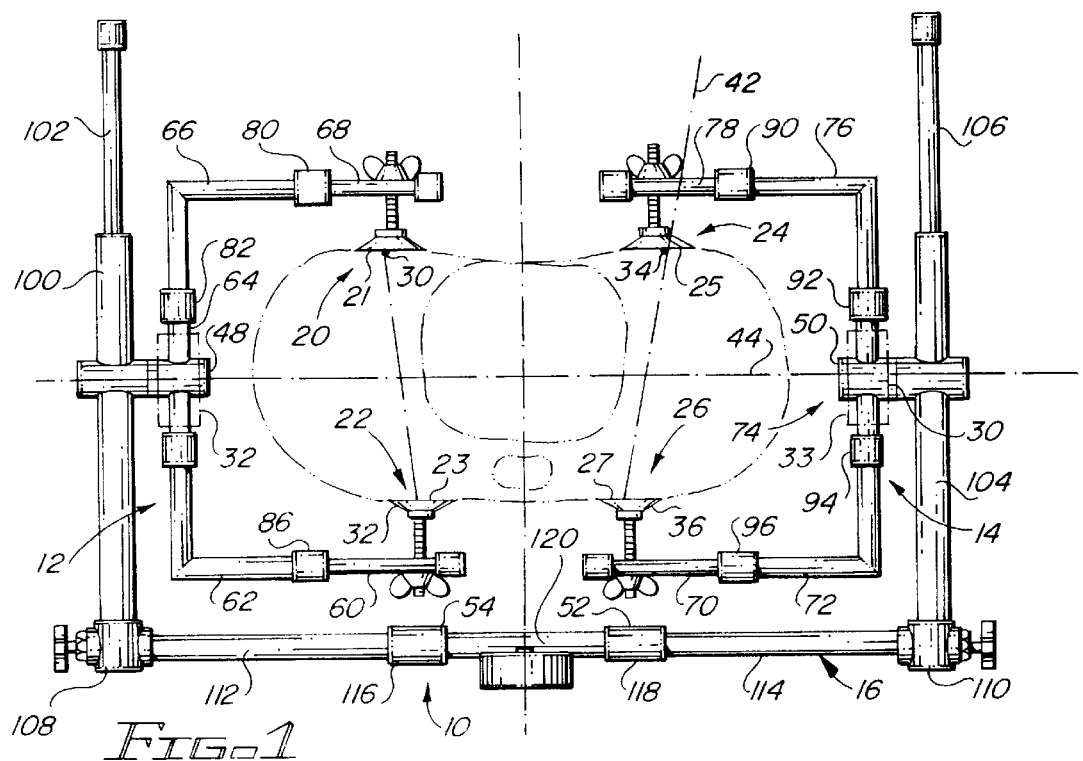
FIG. 1 is a top plan view of the pelvic meter with the pelvis shown in phantom.
Figure 2:
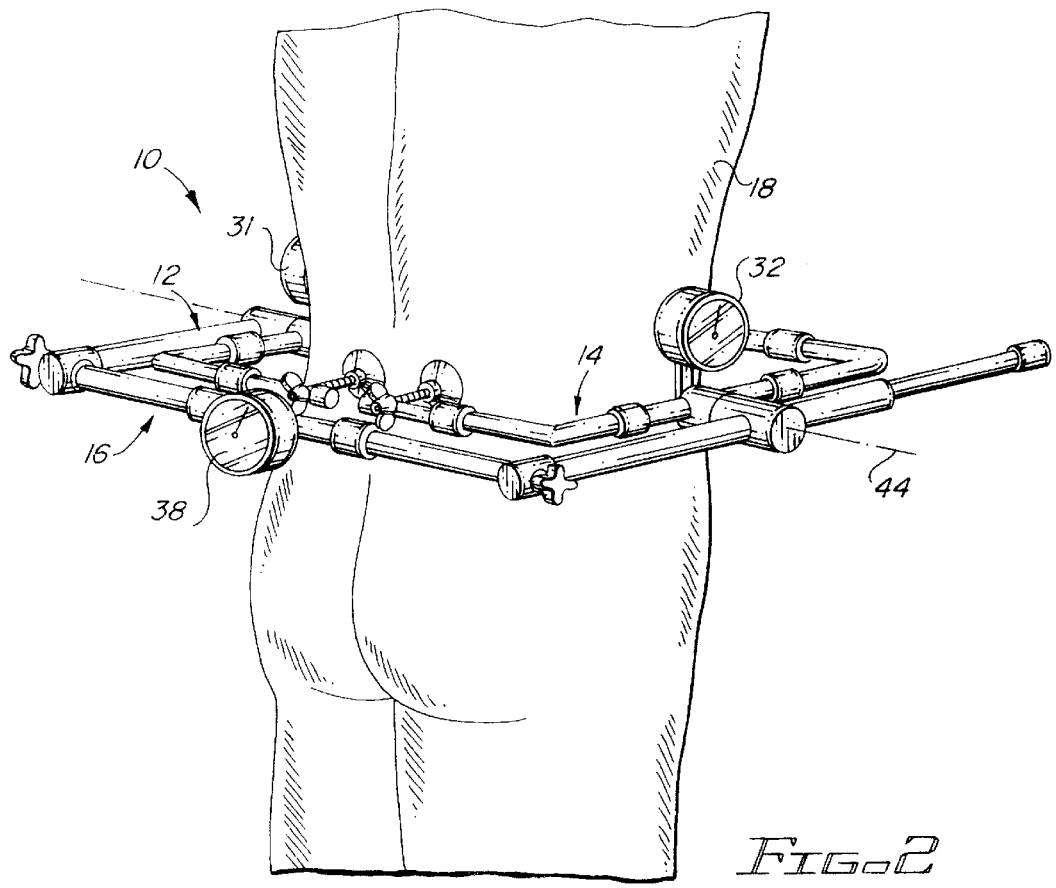
FIG. 2 is a side view of the pelvic meter placed on the subject.

Referring to FIGS. 1 and 2 there is shown a pelvic meter 10 which measures pelvic symmetry. The pelvic meter 10 includes a left U-shaped bracket 12 coupled to a right U-shaped bracket 14 with a rear bracket 16. Bracket 12 and 14 each have an adjustable spring loaded pin mechanism 20,22 and 24,26 respectively to attach to subject 18 with a soft, clear plastic suction cups 21,23, 25 and 27 respectively. Mechanisms 20 and 24 are attached to the left and right ASIS 30, 32 on the subject, and mechanisms 22 and 26 are attached to the left and right PSIS 34 and 36 on the subject respectively. Suction cups 21,23, 25 and 27 permit stability in attachment.

Connected to the center of bracket 12 is fluid goniometer 31 which measures the angle 35 of axis 40 which extends through ASIS 30 and PSIS 32 with respect to the horizon. Connected to the center of bracket 14 is fluid goniometer 33 which measures the angle 37 of axis 42 which extends through ASIS 34 and PSIS 36 with respect to the horizon. Connected to the center of rear bracket 16 is fluid goniometer 38, which is also referred to as an inclinometer, that is disposed about the center of left and right bracket 12 and 14. Goniometer 38 measures the angle 39 of axis 44 extending through points 48 and 50 with respect to the horizon. Angle 35 and 37 are measured in the frontal plane, which is a plane that extends vertically through points located on the right and left side of the body of on a standing subject. Angle 39 is measured in the sagittal plane, which is a plane that extends vertically through points located on the front and back side of the body of on a standing subject.

Pelvic meter 10 is preferably constructed out of aluminum or other lightweight material. Left bracket 12 has telescopic portions 60, 62, 64, 66 and 68, and right bracket 14 has portions 70, 72, 74, 76 and 78. Tightening nobs 80, 82, 84 and 86 on bracket 12, and tightening nobs 90, 92, 94 and 96 on bracket 14 turn to permit portions 60–76 to extend inwards and outwards to enable brackets 12, 14 and 16 to adjust to the body size of subject 18. Goniometer 31 and 33 are attached to the portion 64 and 74 respectively.

Rear bracket has left side outer rod 100 and right side outer rod 104, each having a telescoping inner rod 102 and 106 respectively. Rear bracket has an inner rods 102 and 106 located within outer rods 100 and 104. Outer rods 100 and 104 are respectively connected through tightening device 108 and 110 to rear telescoping rods 112 and 114. Rods 112 and 114 are connected through tightening knobs 116 and 118 to rod 120. Knobs 116 and 118 permit bracket 16 to expend and contract to adjust to the subjects body size. Inner rods 102 and 104 are respectively adjusted with tightening device 108 and 110, located on the rear ends of outer rods 100 and 104. Goniometer 38 is connected to rod 120. Goniometer 30 and 32 are positioned in the sagittal plane with their faces pointing laterally outward. Goniometer 38 is positioned in the frontal plane with its face pointing longitudinally outward.

The rear bracket 16 is connected to portions 64 and 74 respectively on a rotating axel to permit left and right bracket 12 and 14 to pivot on axis 44 with respect to rear bracket 16.

The right, left and rear bracket 12–16, are positioned during use to lye in the horizontal plane around the subject at pelvic level. Tubes 102 and 104 rotate about a sagittal axis 44 to flip up and down in with respect to the horizontal plane to allow the subject to enter the pelvic meter.

While the principles of the invention have been made clear in the illustrated embodiments, there will be immediately obvious to those skilled in the art, many modifications are structured arrangements proportions, elements, materials, and components used in the practice of the invention, in otherwise which are particularly adapted for specific environments and operational requirements, without departing from those principals. The appended claims are therefore intended to cover and embrace any such modifications within the limits only of the true spirit and scope of the invention.

What is claimed is:

1. An apparatus for measuring pelvic symmetry comprising:

a left bracket operative to connect between a left anterior superior iliac spine (ASIS) and a left posterior superior iliac spine (PSIS), said left bracket being connected to means for measuring a first angle of a first axis extending between the left ASIS and left PSIS and the horizon; and a right bracket coupled to the left bracket and operative to connect between a right ASIS and a right PSIS, said right bracket being connected to means for measuring a second angle of an axis extending between of the right ASIS and right PSIS and the horizon, said second angle measuring means permitting measuring while simultaneously measuring the first angle with the first angle measuring means.

2. The apparatus as recited in claim 1 further comprising a center bracket coupling the left bracket to the right bracket having means for measuring the angle of a line extending between the point where the center bracket couples to the left bracket and the point where the center bracket couples to the right bracket and the horizon.

3. The apparatus as recited in claim 1 wherein said means for measuring the first angle of the first axis extending between the left ASIS and left PSIS and the horizon is a fluid goniometer.

4. The apparatus as recited in claim 3 wherein said means for measuring the second angle of the axis extending between of the right ASIS and right PSIS and the horizon is a fluid goniometer.

5. The apparatus as recited 2 wherein said means for measuring the angle of the line extending between the point where the center bracket couples to the left bracket and the point where the center bracket couples to the right bracket and the horizon is a fluid goniometer.

6. An apparatus for measuring pelvic symmetry of a subject comprising:

a left and right u-shaped bracket each having a first pin mechanism attached adjacent one end of the bracket and a second pin mechanism attached adjacent the other end of the bracket, said first pin mechanism operative for attaching to an anterior superior iliac spine point on a subject and said second pin mechanism operative for attaching to a posterior superior iliac spine point on the subject, said brackets each having a goniometer attached about its center portion for measuring the angle of the bracket with respect to the horizon; and a rear u-shaped bracket, having a left portion, center portion and a right portion, said bracket pivotally connected on its right portion to the right u-shaped bracket and pivotally connected on its left portion to the left u-shaped bracket, said rear bracket having a meter connected to its mid portion for measuring the angle of the center portion with respect to the horizon.

7. The apparatus as recited in claim 6 wherein said goniometer is a fluid goniometer.

8. An apparatus for measuring pelvic symmetry comprising:

a left bracket operative to connect between a left anterior superior iliac spine (ASIS) and a left posterior superior iliac spine (PSIS), said left bracket being connected to a first goniometer that measures a first angle of a first axis extending between the left ASIS and left PSIS and the horizon; and a right bracket coupled to the left bracket and operative to connect between a right ASIS and a right PSIS, said right bracket being connected to a second goniometer that measures a second angle of a second axis extending between of the right ASIS and right PSIS and the horizon.

9. The apparatus as recited in claim 8 wherein said goniometers are fluid goniometers.

10. The apparatus as recited in claim 8 further comprising a center bracket connecting the left bracket to the right bracket having a goniometer attached thereto that measures the angle of a line extending between the point where the center bracket connects to the left bracket and the point where the center bracket connects to the right bracket, and the horizon.

* * * * *